United States Patent
Steven

(10) Patent No.: US 9,211,161 B2
(45) Date of Patent: Dec. 15, 2015

(54) APPARATUS AND METHODS FOR ASSOCIATING MEDICAL PROBES WITH CONNECTION PORTS

(71) Applicant: DEPUY SYNTHES PRODUCTS, LLC, Raynham, MA (US)

(72) Inventor: Bittenson N. Steven, Bedford, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 462 days.

(21) Appl. No.: 13/787,227

(22) Filed: Mar. 6, 2013

(65) Prior Publication Data

US 2014/0257046 A1    Sep. 11, 2014

(51) Int. Cl.
| | | |
|---|---|---|
| G08B 1/08 | (2006.01) | |
| A61B 19/00 | (2006.01) | |
| A61B 5/0205 | (2006.01) | |
| A61B 17/32 | (2006.01) | |
| A61B 17/00 | (2006.01) | |

(52) U.S. Cl.
CPC .............. *A61B 19/44* (2013.01); *A61B 5/0205* (2013.01); *A61B 19/56* (2013.01); *A61B 17/320068* (2013.01); *A61B 2017/00225* (2013.01); *A61B 2019/448* (2013.01); *A61B 2562/0257* (2013.01); *A61B 2562/226* (2013.01)

(58) Field of Classification Search
None
See application file for complete search history.

(56) References Cited

U.S. PATENT DOCUMENTS

| | | | |
|---|---|---|---|
| 4,903,340 A * | 2/1990 | Sorensen ...................... 398/117 |
| 5,222,164 A | 6/1993 | Bass, Sr. et al. |
| 5,473,715 A | 12/1995 | Schofield et al. |
| 5,554,049 A * | 9/1996 | Reynolds ...................... 439/490 |
| 5,660,567 A | 8/1997 | Nierlich et al. |
| 5,812,356 A | 9/1998 | O'Connor |
| 6,199,603 B1 * | 3/2001 | DiGianfilippo et al. ........ 141/83 |
| 6,229,420 B1 * | 5/2001 | Bauml et al. .................. 335/205 |
| 6,383,031 B1 * | 5/2002 | Law et al. ...................... 439/680 |
| 6,433,445 B1 | 8/2002 | Ahladas et al. |
| 6,528,746 B2 | 3/2003 | DeWitt et al. |
| 6,560,470 B1 * | 5/2003 | Pologe .......................... 600/310 |
| 6,798,217 B2 * | 9/2004 | Scheible ....................... 324/654 |
| 6,969,928 B2 | 11/2005 | Hanson |
| 7,009,386 B2 | 3/2006 | Tromblee et al. |
| 7,103,698 B2 | 9/2006 | Zhang et al. |
| 7,131,983 B2 * | 11/2006 | Murakami .................... 606/169 |
| 7,319,396 B2 | 1/2008 | Homanfar et al. |
| 7,620,475 B1 | 11/2009 | Bottazzi et al. |
| 7,967,630 B2 * | 6/2011 | Houir Alami ................. 439/490 |
| 2005/0033201 A1 * | 2/2005 | Takahashi et al. ................ 601/2 |
| 2009/0047824 A1 * | 2/2009 | Seibert et al. ................. 439/490 |
| 2011/0012727 A1 * | 1/2011 | Pance et al. ................... 340/505 |
| 2015/0002296 A1 * | 1/2015 | Bell .............................. 340/540 |

* cited by examiner

*Primary Examiner* — Julie Lieu

(57) ABSTRACT

Apparatus, systems and methods for associating medical diagnostic and treatment probes with connection ports of a multiport instrument console. Proximity sensing between a probe and the console provide user-detectable signals indicating the availability or nonavailability of a compatibly configured port for the probe, and specific identification of one or more ports that are compatible with the probe. The proximity sensing also provides capability for identifying and configuring a probe before attempting to connect the probe to a console port.

23 Claims, 3 Drawing Sheets

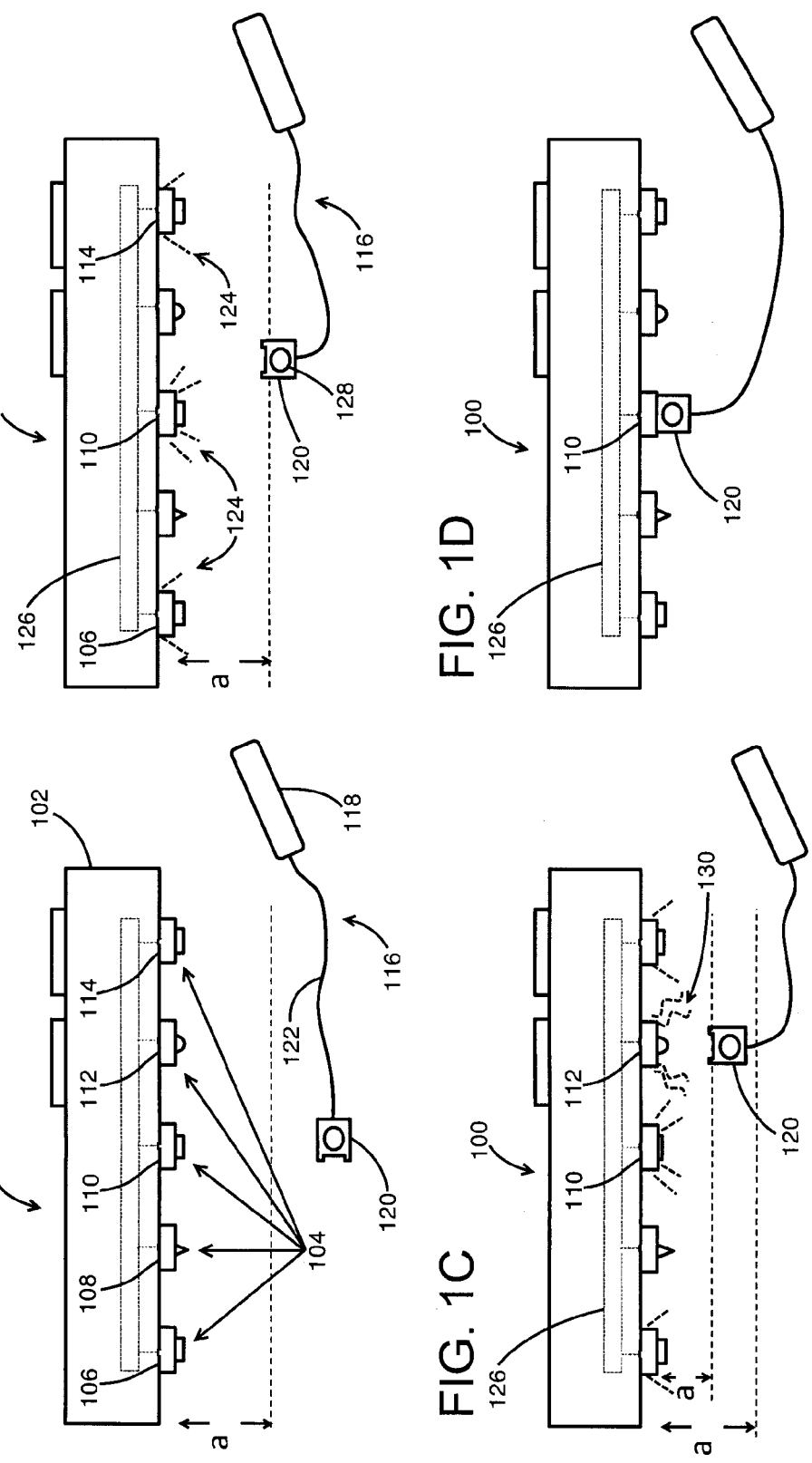

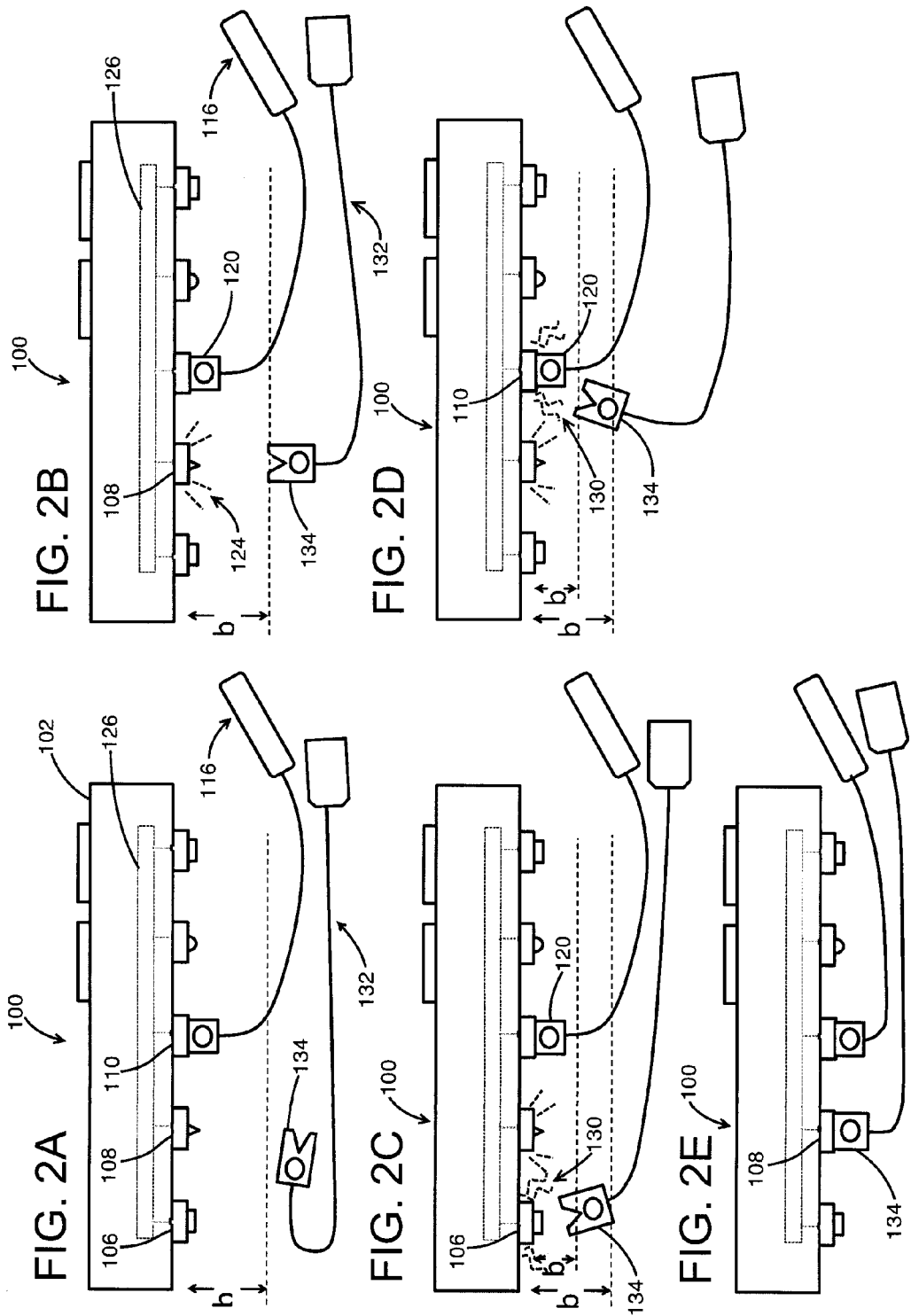

APPARATUS AND METHODS FOR ASSOCIATING MEDICAL PROBES WITH CONNECTION PORTS

FIELD OF THE INVENTION

The invention relates generally to multifunctional medical instrumentation, and more particularly to means for associating medical probes with corresponding functional ports on a multiport medical console.

BACKGROUND OF THE INVENTION

Hospitalized patients often require simultaneous monitoring of several body functions to ensure optimal care. This is especially the case in critical care environments such as surgical and neurocare facilities where, for example, frequent or continuous measurements may be required of intracranial pressure (ICP), oxygen concentrations or partial pressures, temperature, blood pressure, and other functions critical to a patient's recovery or survival. Further, these patients may also require treatment using one or more medical instrument that includes an operative probe connected to a nearby console or instrument controller. The complexity of such multi-technology instrumentation, while generally raising standards of patient care, can also lead to the presence of a large number instruments surrounding and connected to the patient via tubes, wires or cables, making caregiver access to the patient awkward and increasing the likelihood of caregiver error.

Some of this complexity is currently being addressed through the development of multifunctional instrument systems that, for example, may be configured as a multiport console interconnected with two or more medical probes for performing measurements or procedures on the patient. An issue with multifunctional medical instrument systems is that each of a variety of probes must be matched and correctly connected to only a particular corresponding port and not to other ports on a console. These ports may be located relatively close to one another on the console, thereby introducing additional possibilities for error in identifying the correct port for a particular probe. Attempts to incorrectly connect a probe to a console can result in loss of time and potentially damage delicate and expensive medical instruments. Especially in high-stress, time-critical treatment environments such as critical care and surgical facilities, solutions are needed to help minimize such caregiver errors that could potentially harm a patient or lead to damage of delicate and expensive medical equipment.

SUMMARY OF THE INVENTION

One aspect of the present invention is a medical instrument console that includes a plurality of connection ports configured for connection with medical probes that are configured for connection to at least one, but not all of the ports. The medical instrument also includes a proximity detection system for detecting the approach of a probe to the instrument. The proximity detection system detects the presence of a probe connector that is within a first detected distance and generates a first signal that identifies to a user of the instrument any ports that are configured for connection with the probe. If the probe connector is brought within a second, preferably closer distance to an incompatible port or an already occupied port, the proximity detection system generates a second signal distinct from first signal and identifying the unavailability of that port. The proximity detection system can be integral with the console and can also include components such as radio frequency identification tags, integral with or mounted to the probe.

Probes connectable to the console can include medical diagnostic probes and medical treatment probes. Examples of diagnostic probes that can be configured for connection to the console include probes to measure one or more of intracranial pressure, blood pressure, temperature, oxygen, pH, an electrical signal, a chemical composition, an optical signal and an acoustic signal. Medical treatment probes that can be configured for connection to the console include electromechanical instruments, electrosurgical instruments, ultrasonic treatment instruments, optical treatment instruments and a tissue or nerve stimulation instruments. The probes can include a probe body and a connector coupled to one another by a direct physical connection, an electrical cable, a fiber optic cable or a wireless connection.

The proximity sensing system can employ one or more of radio-frequency detection, capacitive detection, optical detection, video detection and magnetic detection. In inventive instruments where radio frequency detection is used, the console includes a radio frequency identification (RFID) transceiver configured to communicate with an RFID tag associated with the probe. For video-based proximity detection, one or more video camera can be integral with the instrument or can be positioned adjacent to one or more of the ports to capture images of a port and a proximate probe. The proximity detection system can also include measurement of the orientation of a probe connector relative to a compatibly configured port.

User-detectable signals generated by the proximity sensing system can include light emission associated with one or more port, a display on a graphical user interface, an acoustic signal, and audio information associated with one or more of a position and an orientation of the probe. The first signal and the second signal can be made distinct from one another in various ways. In one example, the first and the second signal each include light emission and differ from one another with respect to one or more of color, brightness, and time-dependence of the respective light emission. Individual light sources can be provided for each of the ports for generating the signals, and a sound-producing element such as an audio speaker can also be provided to produce a proximity signal. The first signal can provide light of a predetermined color and the probe or the probe connector can be configured to emit light of substantially the same color as that of the first signal.

Another aspect of the present invention is a method for identifying a position of a connector of a medical probe prior to engagement of the connector with a compatible connector port associated with a medical instrument console having a plurality of connector ports. The method comprises detecting proximity of the connector to at least one port of the plurality of ports, generating a user-detectable signal representing the proximity, and generating a second user-detectable signal identifying another connector port of the plurality of ports as incompatible with or unavailable to the probe connector.

Yet another aspect of the present invention is a multifunctional medical instrument system including a console having a plurality of probe-receiving ports and one or more medical probe operable in association with the console. Each of the one or more probe is configured for engagement with at least one of the ports. The system also includes a proximity detection system for detecting a proximity between a probe and the ports, the proximity detection system configured to provide a first user-detectable signal identifying a compatible port. The proximity detection system can also be configured to provide a second user-detectable signal indicating proximity of the probe to a port with which it is incompatible, or which is already occupied by another probe.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various Figures. The drawings are not necessarily to scale, emphasis instead being placed upon illustrating the principles of the invention.

FIGS. 1A through 1D schematically illustrate an exemplary embodiment of a multiport medical instrument according to the present invention, further illustrating a medical probe connector being positioned in proximity to and connected with a compatibly configured port of the instrument.

FIGS. 2A through 2E illustrate an additional probe being positioned in proximity to and connected with the multiport instrument illustrated in FIGS. 1A through 1D.

DETAILED DESCRIPTION

Figure 4A:
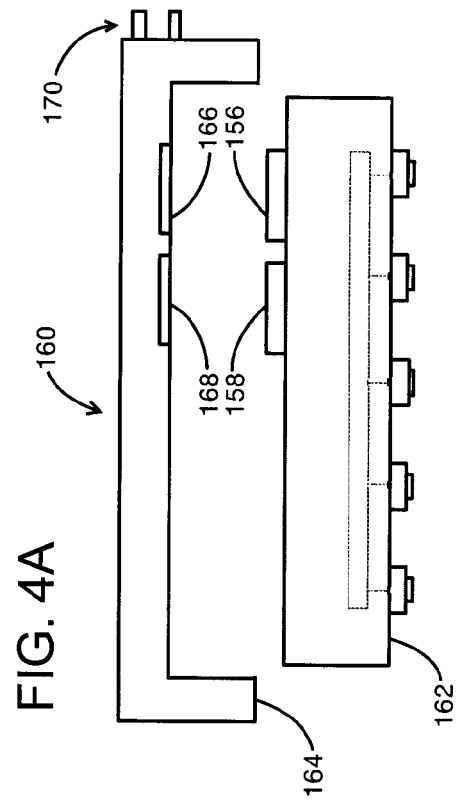
FIGS. 4A and 4B schematically illustrate an embodiment of a multiport instrument according to the present invention comprising a mobile multiport console portion dockable to a base station.

Disclosed herein are medical devices, systems and methods wherein one or more of a plurality of diagnostic or treatment probes is connectable to a multifunctional instrument console, and wherein assistive feedback is provided to a healthcare provider during a process of connecting a probe to the console. Referring more particularly to the Figures, FIG. 1A schematically illustrates an exemplary embodiment of a multiport medical instrument 100 according to the present invention. The instrument 100 is seen to comprise a console 102 having a plurality of probe-receiving ports 104 thereon for connection with respective medical device probes. The plurality of ports 104 comprises at least two ports and can comprise any larger number of ports. The instrument 100 is operable with one or more probe, each connected to a corresponding compatible port. For illustrative purposes only, the console 102 in FIG. 1A is shown as comprising five ports 106, 108, 110, 112, 114 of various configurations. Different configurations are represented schematically in the Figures as different geometrical shapes illustrated with the various ports.

The instrument 100 comprises an interface for at least one of receiving signals from medical diagnostic probes, and controlling medical treatment probes. Many types of medical diagnostic probes and treatment probes are known in this art. Exemplary known diagnostic probes with which the instrument 100 can be configured to interface include probes for measuring one or more of intracranial pressure, blood pressure, temperature, oxygen, pH, a chemical concentration, an electrical signal such as cardiac or neurological diagnostic signals, optical signals, acoustic signals any other signals that can be of use to caregivers, as those skilled in the art will readily recognize. Further examples of diagnostic instruments with which the instrument may be interfaced include visualization devices such as ultrasonic or optical imaging probes.

Exemplary known treatment probes with which the instrument 100 can be configured to interface include electromechanical instruments such as graspers, cutters and manipulators, electrosurgical probes, ultrasonic treatment probes, optical treatment instruments and tissue stimulation probes, such as for electrical stimulation. Typically, different types of diagnostic or treatment probes have different interface requirements for proper operation and employ various types of physical connectors between the probe and a respective controller or console. Even among functionally similar probes, interfaces and connectors often differ incompatibly among different probe manufacturers.

Multifunctional instruments and systems according to the present invention provide feedback to a user during a process of connecting a probe to a port to help a user ensure conveniently that among the plurality of ports and a plurality of probes, only compatibly configured probes are positioned for connection to corresponding ports. FIGS. 1A-1D schematically illustrate an exemplary method according to the present invention of connecting a first probe 116 to a first compatible port 110 of the console 102. First considering FIG. 1A, the first probe 116, which can be any type of probe described herein, is seen to comprise a first probe body 118, a first connector 120 and a communicating means 122 therebetween. In various embodiments known in this art, the communicating means is one or more of an electrical cable, a fiber optic cable, and a conduit for a liquid or a gas. Alternatively, the communicating means is a wireless connection comprising one or more of radio-frequency communication, optical communication, and acoustic communication.

In FIG. 1A, the first connector 120 is shown positioned greater than a first proximity distance "a" from the instrument 100. In various embodiments, the first proximity distance "a" comprises a predetermined physical distance of the first connector 120 from the console 102, from any of the plurality of ports 104, or from one or more compatibly configured ports of the console 102. In other embodiments, the first proximity distance is not a fixed physical distance, but is dependent on the type of probe used. In the illustration of FIG. 1A, the first connector 120 is shown as compatibly configured for connection with any of three ports 106, 110, 114 among the plurality of ports.

The present invention employs proximity sensing between a probe connector and one or more component of the instrument 100. Proximity sensing of one object to another is a known art, with commercially available proximity sensing systems variously employing technologies including, but not limited, to optical sensing, image recognition, capacitive sensing, radio-frequency sensing and acoustic sensing, any of which can be incorporated into embodiments of the present invention. In an embodiment, the proximity sensing further includes lateral position and orientation sensing of the probe with respect to the port. By orientation, we mean relative angular positioning of a probe connector and a compatibly configured port so that an axis of the connector and an axis of the port can be aligned coaxially with one another for connection. In addition, if coupling of the connector to the port requires a preferred rotational angle about the axis, orientation can also refer to identifying the preferred angle. Now turning to FIG. 1B, the first connector is shown positioned within the first proximity distance "a", thereby triggering generation of a first signal of availability 124, represented in the Figures as radiating dashed lines from each respective compatible port 106, 110, 114, by a proximity sensing system 126. Particular ports shown as compatible with probes in the Figures are selected only to illustrate the principles of the invention and are not to be interpreted as limiting of the invention's scope.

The proximity sensing system 126 can be integral with the console 102, and can include elements physically associated or integrated with one or more of the plurality of ports 104. In an embodiment, the proximity sensing system 126 includes one or more remote elements 128 integrated with or mounted to the first probe connector 120. In one embodiment, the one or more remote elements 128 comprise a radio frequency identification (RFID) device. In another embodiment, the one or more remote elements 128 comprise one or more of an optically readable code such as a barcode or a quick-response (QR) code, and an optically reflective element. In another embodiment the one or more remote element 128 functions cooperatively with the proximity sensing system 126 to determine an orientation as well as proximity of the first connector 120 with respect to a closest compatibly configured port 110.

The proximity sensing system 126 generates the user-detectable signal of availability 124 identifying one or more ports 106, 110, 114 as available for connection with the first connector 120. Any type of user-detectable signal is within the scope of the present invention. In one embodiment, as illustrated schematically in FIGS. 1A-1D, each of the plurality of ports 104, or a respective light emitter adjacent thereto, is configured to individually emit light to signal its availability for connection with a compatibly configured probe connector within the first proximity distance "a". Any type of light emitter can be used to generate the signal, including, but not limited to, light-emitting diodes and electroluminescent devices. In another embodiment, the console 102 comprises an emissive or reflective optical image display (not illustrated) adjacent to or about each of the plurality of ports 104 to display the availability of one or more ports for connection to a particular probe positioned within the first proximity distance "a". In yet another embodiment, a remote display such as a computer monitor is used to display the availability of one or more ports for connection to a particular probe when it is positioned within the first proximity distance "a". In still another embodiment, a probe connector includes a light-emitting element such as a light-emitting diode that emits light to confirm a signal of availability. In a further embodiment, the light-emitting element included with the probe connector emits light of a color matching that of the signal of availability.

In the embodiment illustrated in FIG. 1B, each of the compatibly configured ports 106, 110, 114 for receiving the first connector 120 displays the signal of availability 124 via light emission from the respective ports 106, 110, 114. In an embodiment, the available port 110 closest to the first connector 120 when its approach first triggers the proximity sensing system 126 provides a stronger signal of availability, such as brighter illumination, than the signal of availability from the other available ports 106, 114. In another embodiment, only the closest port 110 to the first connector 120 signals its availability. In yet another embodiment, all available ports 106, 110, 114 provide the same signal as one another. In an embodiment, the signal of availability of a port comprises a predetermined color of emitted light. In another embodiment, the signal of availability comprises light having a time-varying intensity or color. In yet another embodiment, the signal of availability comprises one or more of graphics or text on a graphic display.

Now turning to FIG. 1C, the first connector 120 is illustrated as positioned within a second proximity distance "b" of a port 112 that is not compatibly configured for connection with the first connector 120. The second proximity distance "b" is shorter than the first proximity distance "a". The proximity sensing system 126 is seen to respond to this approach to an unavailable port by emitting a user-detectable signal of unavailability 130 such as light emission from or about the unavailable port 112 and comprising a color, intensity or time dependence that distinguishes it from the signal of availability. In an embodiment, the signal of availability includes green-dominated light emission and the signal of unavailability includes red-dominated light emission. In another embodiment the signal of unavailability includes an audible or verbal warning signal generated by the proximity sensing system 126.

FIG. 1D illustrates the first connector 120 connected to the selected compatibly configured port 110. In an embodiment, the proximity sensing system 126 is configured to discontinue generating any proximity signals upon satisfactory connection of a probe to a port. In an embodiment, another signal that is user-distinguishable from either the signal of availability 124 or the signal of unavailability 130 is emitted upon a satisfactory connection between a probe and a port.

Now turning to FIGS. 2A-2E, illustration is provided of a second probe 132 for connection to the console 102. The second probe 132 is configured differently than the first probe 116 and has a second connector 134 that is compatibly configured for connection with at least one port 108 of the plurality of ports 104. As illustrated in FIG. 2A, the proximity sensing system 126 is not responsive to the presence of the second connector 134 outside the first proximity distance "a" and upon approach within the first proximity distance "a" as illustrated in FIG. 2B, the signal of availability 124 is generated associated with the at least one compatibly configured port 108. In another embodiment, a signal of availability associated with the second probe 132 and the second connector 134 is user-distinguishable from the signal of availability 124 associated with the first probe 116 and the first connector 120.

FIG. 2C illustrates the second connector 134 approaching within the second proximity distance "b" of an incompatibly configured port 106, with corresponding generation of the signal of unavailability 130 associated with the incompatibly configured port 106. In this illustration, the unavailable port 106 is a port compatibly configured for the first connector 120. FIG. 2D illustrates the second connector 134 approaching within the second proximity distance "b" of an occupied port 110, illustrated as the port occupied by the first connector 120, with corresponding emission of the signal of unavailability 130. Finally, FIG. 2E illustrates the second connector 134 satisfactorily connected with the compatibly configured port 108.

The illustrative embodiments described above for the behavior of a proximity sensing system used with a multiport, multifunctional instrument system can be varied widely within the principles of the present invention. Within the scope of the present invention are proximity sensing systems that can sense three or more levels of proximity, as well as linear or digital distance measuring systems that can trigger various system behaviors as a function of a measured distance between a probe and a component of the multiprobe system. In addition to discrete proximity sensing systems, one or more video camera integrated with or positioned nearby a multiport console according to the present invention can provide the input for a proximity or distance measuring system between probes and a console via image recognition software. In an embodiment, video signal analysis is also used to provide lateral positioning and orientation information for guiding a probe to a port.

Software and other control systems of the inventive apparatus and system can also be widely varied within the principles of the invention. For example, a probe of unrecognized configuration sensed as entering within a first proximity distance can immediately trigger a signal of unavailability. Alternatively, such an unrecognized entry can initiate execution of software to attempt to identify the unrecognized probe or attempt to configure the probe for compatibility with an unoccupied port, with or without interactive input from a user or via a communications network connection.

Figure 3:
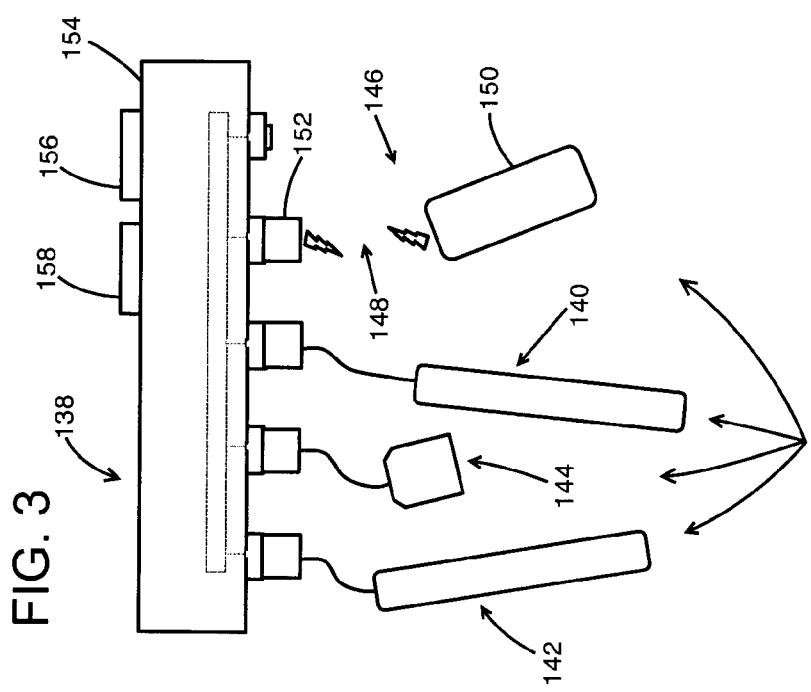
FIG. 3 schematically illustrates a plurality of probes connected to a multiport instrument according to the present invention.

FIG. 3 schematically illustrates a plurality of probes 136 connected to a multiport instrument 138 according to the present invention, including two cable-connected probes 140, 142 of a first configuration, one cable-connected probe 144 of a second configuration, and another probe 146 having a wireless connection 148 between a wireless probe body 150 and a wireless probe connector 152 configured for connection with a compatible port on a console 154.

An instrument according to the present invention can be powered by any compatible means, including one or both of externally powered via a conductive or inductive electrical connection 156, and internally powered using battery or capacitor storage that can in an embodiment be rechargeable via the electrical connection 156. An instrument according to the present invention can include on-board computing capability to process, integrate and display diagnostic data or treatment instrument parameters. In an embodiment, the display is integral with the console 154. The instrument can also include a wired or wireless interface 158 for connection to one or more of an external display, an external computer and an external communications network. In another embodiment, the interface 158 also provides one or more of gas, liquid, and vacuum connections for delivery via the console 154 to one or more compatible probes.

Figure 4B:
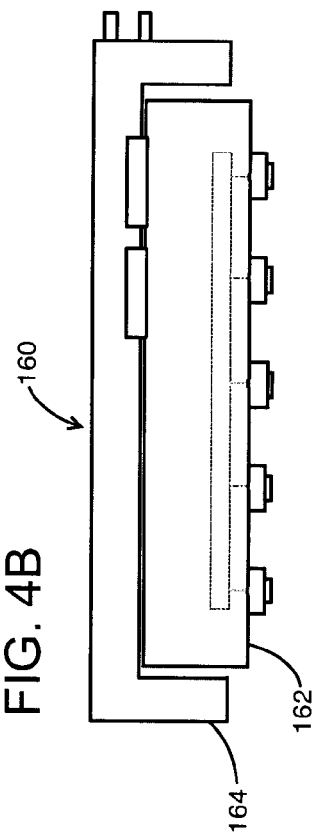

FIGS. 4A and 4B schematically illustrate an embodiment of a multiport instrument 160 according to the present invention comprising a mobile multiport console portion 162 dockable to a base station 164. Base station 164 provides stationary connections 166, 168 for at least one of respective power and communications interfaces 156, 158 for console 162. FIG. 4A illustrates console 162 undocked from the base station 164, for example, for transport of the console 162 with a patient between facilities. FIG. 4B illustrates console 162 docked with the base station 164. In an embodiment, base station 164 also provides access portals 170 to one or more of stationary gas, liquid and vacuum sources, as well as to utility power and communications connections. Inclusion of the base station 164 is particularly useful where a patient must be moved between rooms or between medical facilities and disconnection of a plurality of probes from the patient would be undesirable. Preferably, console 162 includes adequate internal energy storage for continued operation during transport, until docked in the same or another base station.

Advantageously, multiport instruments and systems according to the present invention provide improved usability compared with prior multiport instruments and systems by indicating to a user whether and exactly where on a multiport console a medical probe can be safely and effectively connected. This improvement is of particular utility in critical care or surgical environments where many medical devices may be connected to a patient and both accurate and timely actions by medical professionals are of great importance to the condition of the patient. In addition, the present invention enables less-skilled assistants than might otherwise be required to reliably set up instruments for use with patients. With the addition of one or both of lateral position sensing and orientation sensing of a probe connector with respect to a port, further improvements in utility and reliability are provided.

Also advantageously, by warning a user that a port and an instrument are incompatible before the components are placed in physical contact with one another, the present invention is expected to greatly reduce the number of instances of attempted and potentially damaging coupling of incompatible devices. Further, embodiments according to the present invention provide the user with an opportunity to determine in realtime whether a probe can be configured for use with a console, and provide assistance with such configuration before the probe is connected to a port of the console. Even further, embodiments according to the present invention wherein a probe includes an identification element readable by the proximity sensing system, a medical facility or a supervisory medical professional can customize the readable element to provide notice of preferred configurations or uses of a particular probe or type of probe.

While the invention has been particularly shown and described with reference to specific preferred embodiments, it should be understood by those skilled in the art that various changes in form and detail may be made therein without departing from the spirit and scope of the invention as defined by the appended claims.

What is claimed is:
1. A medical instrument comprising:
 a console having a plurality of probe connection ports thereon, a first one of the plurality of ports configured for connection with a first connector associated with a first medical probe that is configured for engagement with the first port and not configured for connection with a second one of the plurality of ports;
 a proximity detection system configured to generate a first proximity signal upon positioning of the first connector within a first proximity to at least one of the first port, the plurality of ports and the console; the proximity detection system configured to generate a second signal upon positioning of the first connector within a second proximity to the second port, the second signal being distinct from the first signal; and wherein the second proximity corresponds to a shorter physical distance than the first proximity.

2. The instrument according to claim 1 wherein at least a portion of the proximity detection system is integral with the console.

3. The instrument according to claim 1 wherein the proximity detection system further comprises a component one of mounted to and integral with the first probe.

4. The instrument according to claim 1 wherein the first probe is at least one of a medical diagnostic probe and a medical treatment probe.

5. The instrument according to claim 4 wherein the medical diagnostic probe is configured to measure one or more of intracranial pressure, blood pressure, temperature, oxygen, pH, an electrical signal, a chemical composition, an optical signal and an acoustic signal.

6. The instrument according to claim 4 wherein the medical treatment probe is one or more of an electromechanical instrument, an electrosurgical instrument, an ultrasonic treatment instrument, an optical treatment instrument and a tissue stimulation instrument.

7. The instrument according to claim 1 wherein the first probe comprises a probe body and the first connector, the probe body and the first connector being coupled to one another by one or more of a direct physical connection, an electrical cable, a fiber optic cable and a wireless connection.

8. The instrument according to claim 1 wherein the proximity sensing system comprises one or more of radio-frequency detection, capacitive detection, optical detection, video detection and magnetic detection.

9. The instrument according to claim 8 wherein the radio frequency detection comprises a radio frequency identification transceiver configured to communicate with a radio frequency identification tag associated with the first probe.

10. The instrument according to claim 8 wherein the video detection comprises a video camera one of adjacent to and integral with one or more of the ports and positioned to capture images of at least one of the first port and a proximate probe.

11. The instrument according to claim 1, further comprising orientation detection configured to determine at least one of a relative axial orientation and a rotational orientation about a mutual axis of a connector component of the first probe relative to the first port.

12. The instrument according to claim 1 wherein at least one of the first signal and the second signal comprises one or more of light emission associated with the respective port, a display on a graphical user interface, an acoustic signal, and audio information associated with one or more of a position and an orientation of the first probe.

13. The instrument according to claim 12 wherein the first signal and the second signal comprise light emission and differ from one another with respect to one or more of color, brightness, and time-dependence of the respective light emission.

14. The instrument according to claim 1 wherein further each of the plurality of ports is individually associated with each of the plurality of ports, and an audio speaker.

15. The instrument according to claim 13 wherein the first signal comprises light of a first predetermined color and a component of the probe is configured to emit light of substantially the first predetermined color.

16. The instrument according to claim 15 wherein the second signal comprises light of a second predetermined color and a component of the probe is configured to emit light of substantially the second predetermined color, the first predetermined color being different than the second predetermined color.

17. The instrument according to claim 1 wherein at least one of the first and the second signal further comprises signaling a presence of a second probe connected to the first port.

18. A multifunctional medical instrument system comprising:
- a console having a plurality of connection ports associated therewith, each of the plurality of ports configured for connection with a compatibly configured medical probe;
- at least two medical probes operable in association with the console and configured for compatible connection with at least one port among the plurality of ports;
- a proximity sensing system for detecting a proximity between one of the at least two medical probes and at least one of the plurality of ports, the proximity sensing system configured to provide a first user-detectable signal indicating a location of the at least one compatible port;
- wherein the proximity sensing system is further configured to provide a second user-detectable signal indicating one or more of proximity of the at least two medical probes to a port incompatible therewith, and a presence of another medical probe previously connected to the at least one compatible port.

19. The system according to claim 18 wherein the proximity sensing system comprises one or more of radio-frequency detection, capacitive detection, optical detection, video detection and magnetic detection.

20. A multiport bedside monitor configured for receiving one or more medial probes for monitoring a body function of a patient, each of the one or more probes having a respective connector associated therewith, the monitor comprising:
- a console having a plurality of medical probe connection ports thereon, the monitor configured to generate a first visually perceptible optical signal upon the positioning of a first probe connector less than a first distance from a first portion of the console, the first signal indicating a first port configured for receiving the first connector, the monitor further configured to generate a second optical signal visually distinct from the first signal upon the positioning of the first probe connector less than a second distance from a second port that is not configured for receiving the first connector, the second distance being shorter than the first distance.

21. The monitor according to claim 20 wherein the first signal comprises green light emitted at least one of from and adjacent to the first port, and the second signal comprises at least one of differently colored light emission and pulsed light emission.

22. The monitor according to claim 20 wherein the second signal comprises an acoustic signal.

23. A medical instrument comprising:
a) a console having a plurality of probe connection ports thereon, a first one of the plurality of ports configured for connection with a first connector associated with a first medical probe that is configured for engagement with the first port and not configured for connection with a second one of the plurality of ports;
b) a proximity detection system configured to detect a first proximity upon positioning of the first connector within a first distance to one of the first port, the plurality of ports and the console, the proximity detection system configured to detect a second proximity upon positioning of the first connector within a second distance to the second port, the second distance being shorter than the first distance; and
c) a signal generation system configured to generate a first signal upon detection of the first proximity, the first signal including at least one of a first optical emission and a first visual display on a graphical user interface, the signal generation system configured to generate a second signal distinct from the first signal upon detection of the second proximity, the second signal including at least one of a second optical emission, a second visual display on the graphical user interface, and an acoustic signal.

* * * * *